US005932425A

United States Patent [19]
Alkalay et al.

[11] Patent Number: 5,932,425
[45] Date of Patent: Aug. 3, 1999

[54] COMPOSITIONS AND METHODS FOR MODULATING CELLULAR NF-κB ACTIVATION

[75] Inventors: Irit Alkalay, Jerusalem; Yinon Ben-Neriah, Zion; Aaron Ciechanover, Haifa, all of Israel; Anthony Manning; Frank Mercurio, both of San Diego, Calif.; Avraham Yaron, Jerusalem, Israel

[73] Assignees: Signal Pharmaceuticals, Inc., San Diego, Calif.; Yissum Research Development Company of the Hebrew University of Jerusalem, Jerusalem, Israel

[21] Appl. No.: 08/802,322

[22] Filed: Feb. 18, 1997

[51] Int. Cl.$^6$ .......................... G01N 33/53; A01N 37/18; A61K 38/00; C12Q 1/00
[52] U.S. Cl. .................................. 435/7.1; 435/4; 514/2; 530/300; 530/326; 530/327; 530/328
[58] Field of Search .................................. 435/4, 7.1, 15, 435/194; 530/300, 326, 327, 328; 514/2

[56] References Cited

FOREIGN PATENT DOCUMENTS

| 2112193 | 6/1994 | Canada . |
| 603 672 A2 | 6/1994 | European Pat. Off. . |
| WO 91/18096 | 11/1991 | WIPO . |
| WO 98/08955 | 3/1998 | WIPO . |

OTHER PUBLICATIONS

Alkalay et al., "Stimulation–dependent IκBα phosphorylation marks the NF–κB inhibitor for degradation via the ubiquitin–proteasome pathway," *Proc. Natl. Acad. Sci. USA* 92: 10599–10603, 1995.
Chen et al., "Selective Inhibition of E–Selectin, Vascular Cell Adhesion Molecule–1, and Intercellular Adhesion Molecule–1 Expression by Inhibitors of IκB–α Phosphorylation," *The Journal of Immunology* 155: 3538–3545, 1995.
Chen et al., "Signal–induced site–specific phosphorylation targets IκBα to the ubiquitin–proteasome pathway," *Genes & Development* 9: 1586–1597, 1995.
Ciechanover et al., "The Ubiquitin–mediated Proteolytic System: Involvement of Molecular Chaperones, Degradation of Oncoproteins, and Activation of Transcriptional Regulators," *Cold Spring Harbor Symposia on Quantitative Biology* 60: 491–501, 1995.
Ciechanover, "The Ubiquitin–Proteasome Proteolytic Pathway," *Cell* 79: 13–21, 1994.
Yaron et al., "Inhibition of NF–κB cellular function via specific targeting of the IκB–ubiquitin ligase," *The EMBO Journal* 16(21): 6486–6494, 1997.
Aberle et al., "β–catenin is a target for the ubiquitin–proteasome pathway," *The EMBO Journal* 16(13): 3797–3804, 1997.
Baeuerle and Baltimore, "NF–κB: Ten Years After," *Cell* 87: 13–20, 1996.

Baldi et al., "Critical Role for Lysines 21 and 22 in Signal–induced, Ubiquitin–mediated Proteolysis of IκB–α," *The Journal of Biological Chemistry* 271(1): 376–379, 1996.
Baldwin, Jr., "The NF–κB And IκB Proteins: New Discoveries and Insights," *Annu. Rev. Immunol.* 14: 649–681, 1996.
Brockman et al., "Coupling of a Signal Response Domain in IκBα to Multiple Pathways for NF–κB Activation," *Molecular and Cellular Biology* 15(5): 2809–2818, 1995.
Brown et al., "Control of IκB–α Proteolysis by Site–Specific, Signal–Induced Phosphorylation," *Science* 267: 1485–1488, 1995.
Deshaies, "Make it or break it: the role of ubiquitin–dependent proteolysis in cellular regulation," *Trends In Cell Biology* 5: 428–434, 1995.
DiDonato et al., "Mapping of the Inducible IκB Phosphorylation Sites That Signal its Ubiquitination and Degradation," *Molecular and Cellular Biology* 16(4): 1295–1304, 1996.
Dohmen et al., "The N–end rule is mediated by the UBC2(RAD6) ubiquitin–conjugating enzyme," *Proc. Natl. Acad. Sci. USA* 88: 7351–7355, 1991.
Gonen et al., "Isolation, Characterization, and Partial Purification of a Novel Ubiquitin–Protein Ligase, E3," *The Journal Of Biological Chemistry* 271(1): 302–310, 1996.
Hein et al., "NPI1, an essential yeast gene involved in induced degradation of Gap1 and Fur4 permeases, encodes the Rsp5 ubiquitin–protein ligase," *Molecular Microbiology* 18(1): 77–87, 1995.
Hershko and Ciechanover, "The Ubiquitin System For Protein Degradation," *Ann. Rev. Biochem.* 61: 761–807, 1992.
Hochstrasser, "Ubiquitin, proteasomes, and the regulation of intracellular protein degradation," *Current Opinion in Cell Biology* 7: 215–223, 1995.
Huibregtse et al., "A family of proteins structurally and functionally related to the E6–AP ubiquitin–protein ligase," *Proc. Natl. Acad. Sci. USA* 92: 2563–2567, 1995.
Jentsch and Schlenker, "Selective Protein Degradation: A Journey's End within the Proteasome," *Cell* 82: 881–884, 1995.
King et al., "A 20S Complex Containing CDC27 and CDC16 Catalyzes the Mitosis–Specific Conjugation of Ubiquitin to Cyclin B," *Cell* 81: 279–288, 1995.
Lam et al., "A new type of synthetic peptide library for identifying ligand–binding activity," *Nature* 354:82–84, 1991.

(List continued on next page.)

*Primary Examiner*—Nancy Degen
*Attorney, Agent, or Firm*—Seed and Berry LLP

[57] ABSTRACT

Compositions and methods for modulating the activation of nuclear factor κB (NF-κB) are provided. The compositions comprise one or more agents that modulate ubiquitination of phosphorylated IκBα and/or IκBβ. Such compositions may be used for treating diseases associated with NF-κB activation. Modulating agents include peptides that comprise a recognition domain for E3 ubiquitin ligase.

7 Claims, 7 Drawing Sheets

OTHER PUBLICATIONS

Mercurio et al., "p105 and p98 precursor proteins play an active role in the NF–κB–mediated signal transduction," *Genes & Development* 7: 705–718, 1993.

Nefsky and Beach, "Pub1 acts as an E6–AP–like protein ubiquitin ligase in the degradation," *The EMBO Journal* 15(6): 1301–1312, 1996.

Nuber et al., "Cloning of Human Ubiquitin–conjugating Enzymes UbcH6 and UbcH7 (E2–F1) and Characterization of Their Interaction with E6–AP and RSP," *The Journal of Biological Chemistry* 271: 2795–2800, 1996.

Orian et al., "Ubiquitin–mediated Processing of NF–κB Transcriptional Activator Precursor p105," *The Journal Of Biological Chemistry* 270: 21707–21714, 1995.

Read et al., "The Proteasome Pathway Is Required for Cytokine–Induced Endothelial–Leukocyte Adhesion Molecule Expression," *Immunity* 2: 493–506, 1995.

Reiss and Hershko, "Affinity Purification of Ubiquitin–Protein Ligase on Immobilized Protein Substrates," *The Journal of Biological Chemistry* 265(7): 3685–3690, 1990.

Scheffner et al., "The HPV–16 E6 and E6–AP Complex Functions as a Ubiquitin–Protein Ligase in the Ubiquitination of p53," *Cell* 75: 495–505, 1993.

Scherer et al., "Signal–induced degradation of IκBα requires site–specific ubiquitination," *Proc. Natl. Acad. Sci. USA* 92: 11259–11263, 1995.

Stancovski et al., "Degradation of the Proto–Oncogene Product c–Fos by the Ubiquitin Proteolytic System In Vivo and In Vitro: Identification and Characterization of the Conjugating Enzymes," *Molecular and Cellular Biology* 15(12): 7106–7116, 1995.

Staub et al., "WW domains of Nedd4 bind to the proline–rich PY motifs in the epithelial $Na^{30}$ channel deleted in Liddle's syndrome," *The EMBO Journal* 15(10): 2371–2380, 1996.

Sun et al., "Both Amino–and Carboxyl–Terminal Sequences within IκBα Regulate Its Inducible Degradation," *Molecular and Cellular Biology* 16: 1058–1065, 1996.

Thompson et al., "IκB–α Regulates the Persistent Response in a Biphasic Activation of NF–κB," *Cell* 80: 573–582, 1995.

Traenckner et al., "Phosphorylation of human IκB–α on serines 32 and 36 controls IκB–α proteolysis and NF–κB activation in response to diverse stimuli," *The EMBO Journal* 14(12): 2876–2883, 1995.

Varshavsky, "The N–End Rule," *Cell* 69: 725–735, 1992.

Verma et al., "Rel/NF–κB/IκB family: intimate tales of association and dissociation," *Genes & Development* 9: 2723–2735, 1995.

Whiteside et al., "N–and C–Terminal Sequences Control Degradation of MAD3/IκBα in Response to Inducers of NF–κB Activity," *Molecular and Cellular Biology* 15(10): 5339–5345, 1995.

Willems et al., "Cdc53 Targets Phosphorylated G1 Cyclins for Degradation by the Ubiquitin Proteolytic Pathway," *Cell* 86: 453–463, 1996.

Chen et al. Site–Specific Phosphorylation of IkBa by a Novel Ubiquitination–Dependent Protein Kinase Activity. Cell. 84: 853–862, Mar. 22, 1996.

Rodriguez et al. Identification of Lysine Residues Required for Signal–Induced Ubiquitination and Degradation of IkBa In Vivo. Oncogene. 12: 2425–2435, 1996.

Scherer et al. Signal–Induced Degradation of IkBa Required Site–Specific Ubiquitination. Proc. Natl. Acad. Sci. 92: 11259–11263, 1995.

Roff et al. Role of IkBa Ubiquitination in Signal–Induced Activation of NF–kB in Vivo. J. Biol. Chem. 271 (13): 7844–7850, Mar. 29, 1996.

Chen et al. Signal–Induced Site–Specific Phosphorylation Targets IkBa to the Ubiquitin–Proteasome Pathway. Genes & Devel. 9: 1586–1597, 1995.

Li et al. Inactivation of NF–kB Inhibitor IkBa: Ubiquitin–Dependent Proteolysis and its Degradation Product. 215 (1): 292–301, Oct. 4, 1995.

```
                          SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 317 amino acids
        (B) TYPE: amino acid
        (C) STRANDEDNESS:
        (D) TOPOLOGY: linear (xi) SEQUENCE DESCRIPTION: SEQ ID NO:1:

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Val Pro Arg Gly Ser Glu
    50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Leu Gly Gln Leu
            260                 265                 270

Thr Leu Glu Asn Leu Gln Met Leu Pro Glu Ser Glu Asp Glu Glu Ser
        275                 280                 285
```

```
Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315
```

(2) INFORMATION FOR SEQ ID NO:2:

(i) SEQUENCE CHARACTERISTICS:
        (A) LENGTH: 1550 base pairs
        (B) TYPE: nucleic acid
        (C) STRANDEDNESS: single
        (D) TOPOLOGY: linear (xi) SEQUENCE DESCRIPTION: SEQ ID NO:2:

```
TGCCGCCGTC CCGCCCGCCA GCGCCCCAGC GAGGAAGCAG CGCGCAGCCC GCGGCCCAGC    60

GCACCCGCAG CAGCGCCCGC AGCTCGTCCG CGCCATGTTC CAGGCGGCCG AGCGCCCCCA   120

GGAGTGGGCC ATGGAGGGCC CCCGCGACGG GCTGAAGAAG GAGCGGCTAC TGGACGACCG   180

CCACGACAGC GGCCTGGACT CCATGAAAGA CGAGGAGTAC GAGCAGATGG TCAAGGAGCT   240

GCAGGAGATC CGCCTCGAGC CGCAGGAGGT GCCGCGCGGC TCGGAGCCCT GGAAGCAGCA   300

GCTCACCGAG GACGGGGACT CGTTCCTGCA CTTGGCCATC ATCCATGAAG AAAAGGCACT   360

GACCATGGAA GTGATCCGCC AGGTGAAGGG AGACCTGGCT TTCCTCAACT TCCAGAACAA   420

CCTGCAGCAG ACTCCACTCC ACTTGGCTGT GATCACCAAC CAGCCAGAAA TTGCTGAGGC   480

ACTTCTGGGA GCTGGCTGTG ATCCTGAGCT CCGAGACTTT CGAGGAAATA CCCCCCTACA   540

CCTTGCCTGT GAGCAGGGCT GCCTGGCCAG CGTGGGAGTC CTGACTCAGT CCTGCACCAC   600

CCCGCACCTC CACTCCATCC TGAAGGCTAC CAACTACAAT GGCCACACGT GTCTACACTT   660

AGCCTCTATC CATGGCTACC TGGGCATCGT GGAGCTTTTG GTGTCCTTGG GTGCTGATGT   720

CAATGCTCAG GAGCCCTGTA ATGGCCGGAC TGCCCTTCAC CTCGCAGTGG ACCTGCAAAA   780

TCCTGACCTG GTGTCACTCC TGTTGAAGTG TGGGGCTGAT GTCAACAGAG TTACCTACCA   840

GGGCTATTCT CCCTACCAGC TCACCTGGGG CCGCCCAAGC ACCCGGATAC AGCAGCAGCT   900

GGGCCAGCTG ACACTAGAAA ACCTTCAGAT GCTGCCAGAG AGTGAGGATG AGGAGAGCTA   960

TGACACAGAG TCAGAGTTCA CGGAGTTCAC AGAGGACGAG CTGCCCTATG ATGACTGTGT  1020

GTTTGGAGGC CAGCGTCTGA CGTTATGAGT GCAAAGGGGC TGAAAGAACA TGGACTTGTA  1080

TATTTGTACA AAAAAAAAGT TTTATTTTTC TAAAAAAAGA AAAAGAAGA  AAAAATTTAA  1140

AGGGTGTACT TATATCCACA CTGCACACTG CCTAGCCCAA AACGTCTTAT TGTGGTAGGA  1200

TCAGCCCTCA TTTTGTTGCT TTTGTGAACT TTTTGTAGGG GACGAGAAAG ATCATTGAAA  1260

TTCTGAGAAA ACTTCTTTTA AACCTCACCT TTGTGGGGTT TTTGGAGAAG GTTATCAAAA  1320

ATTTCATGGA AGGACCACAT TTTATATTTA TTGTGCTTCG AGTGACTGAC CCCAGTGGTA  1380

TCCTGTGACA TGTAACAGCC AGGAGTGTTA AGCGTTCAGT GATGTGGGGT GAAAAGTTAC  1440

TACCTGTCAA GGTTTGTGTT ACCCTCCTGT AAATGGTGTA CATAATGTAT TGTTGGTAAT  1500

TATTTTGGTA CTTTTATGAT GTATATTTAT TAAAGAGATT TTTACAAATG             1550
```

(2) INFORMATION FOR SEQ ID NO:3:

(i) SEQUENCE CHARACTERISTICS:
        (A) LENGTH: 359 amino acids
        (B) TYPE: amino acid
        (C) STRANDEDNESS:
        (D) TOPOLOGY: linear (xi) SEQUENCE DESCRIPTION: SEQ ID NO:3:

Met Ala Gly Val Ala Cys Leu Gly Lys Thr Ala Asp Ala Asp Glu Trp
1               5                   10                  15

Cys Asp Ser Gly Leu Gly Ser Leu Gly Pro Asp Ala Ala Pro Gly
            20                  25                  30

Gly Pro Gly Leu Gly Ala Glu Leu Gly Pro Glu Leu Ser Trp Ala Pro
        35                  40                  45

Leu Val Phe Gly Tyr Val Thr Glu Asp Gly Asp Thr Ala Leu His Leu
    50                  55                  60

Ala Val Ile His Gln His Glu Pro Phe Leu Asp Phe Leu Leu Gly Phe
65              70                  75                  80

Ser Ala Gly His Glu Tyr Leu Asp Leu Gln Asn Asp Leu Gly Gln Thr
                85                  90                  95

Ala Leu His Leu Ala Ala Ile Leu Gly Glu Ala Ser Thr Val Glu Lys
                100                 105                 110

Leu Tyr Ala Ala Gly Ala Gly Val Leu Val Ala Glu Arg Gly Gly His
        115                 120                 125

Thr Ala Leu His Leu Ala Cys Arg Val Arg Ala His Thr Cys Ala Cys
    130                 135                 140

Val Leu Leu Gln Pro Arg Pro Ser His Pro Arg Asp Ala Ser Asp Thr
145                 150                 155                 160

Tyr Leu Thr Gln Ser Gln Asp Cys Thr Pro Thr Ser His Ala Pro
                165                 170                 175

Ala Ala Val Asp Ser Gln Pro Asn Pro Glu Asn Glu Glu Pro Arg
            180                 185                 190

Asp Glu Asp Trp Arg Leu Gln Leu Glu Ala Glu Asn Tyr Asp Gly His
            195                 200                 205

Thr Pro Leu His Val Ala Val Ile His Lys Asp Ala Glu Met Val Arg
    210                 215                 220

Leu Leu Arg Asp Ala Gly Ala Asp Leu Asn Lys Pro Glu Pro Thr Cys
225                 230                 235                 240

Gly Arg Thr Pro Leu His Leu Ala Val Glu Ala Gln Ala Ala Ser Val
            245                 250                 255

Leu Glu Leu Leu Leu Lys Ala Gly Ala Asp Pro Thr Ala Arg Met Tyr
            260                 265                 270

Gly Gly Arg Thr Pro Leu Gly Ser Ala Leu Leu Arg Pro Asn Pro Ile
        275                 280                 285

Leu Ala Arg Leu Leu Arg Ala His Gly Ala Pro Glu Pro Glu Asp Glu
    290                 295                 300

Asp Asp Lys Leu Ser Pro Cys Ser Ser Ser Gly Ser Asp Ser Asp Ser
305                 310                 315                 320

Asp Asn Arg Asp Glu Gly Asp Glu Tyr Asp Asp Ile Val Val His Ser
            325                 330                 335

Gly Arg Ser Gln Asn Arg Gln Pro Pro Ser Pro Ala Ser Lys Pro Leu
            340                 345                 350

Pro Asp Asp Pro Asn Pro Ala
            355

(2) INFORMATION FOR SEQ ID NO:4:

(i) SEQUENCE CHARACTERISTICS:
        (A) LENGTH: 1212 base pairs
        (B) TYPE: nucleic acid
        (C) STRANDEDNESS: single
        (D) TOPOLOGY: linear (xi) SEQUENCE DESCRIPTION: SEQ ID NO:4:

```
GCGCACTGGA GCTCATCGCA GAGCCCAGCG ACAGGCAGGC GACCACAGGG GGCCACCCGA      60

GGTGGCTGGG GCCATGGCCG GGGTCGCGTG CTTGGGGAAA ACTGCGGATG CCGATGAATG     120

GTGCGACAGC GGCCTGGGCT CTCTAGGTCC CGACGCAGCG GCTCCCGGAG GACCAGGTCT     180

GGGCGCAGAG CTTGGCCCAG AGCTGTCGTG GGCGCCCTTA GTCTTTGGCT ACGTCACTGA     240

GGATGGGGAC ACAGCCCTGC ACTTGGCTGT GATTCATCAG CATGAGCCCT TCCTGGATTT     300

CCTCCTGGGC TTTTCCGCCG CCACGAGTA CCTTGACCTG CAGAATGACC TAGGCCAAAC      360

AGCCCTGCAT CTAGCAGCCA TCCTTGGGGA GGCATCTACA GTAGAGAAGT TGTATGCAGC     420

CGGTGCAGGA GTGTTGGTGG CTGAGAGAGG GGGCCACACG GCATTGCACT TGGCCTGCCG     480

GGTCAGGGCA CACACGTGCG CGTGCGTACT GCTCCAGCCC CGTCCCAGCC ACCCAAGAGA     540

TGCCTCAGAT ACCTACCTCA CTCAGAGCCA GGACTGTACC CCAGACACCA GCCATGCCCC     600

TGCTGCCGTG GATTCCCAAC CCAACCCAGA GAACGAAGAG GAGCCGCGTG ATGAAGACTG     660

GAGGCTACAA CTAGAAGCTG AAAACTATGA TGGCCATACC CCACTCCATG TAGCTGTCAT     720

CCACAAAGAT GCAGAGATGG TCCGGCTGCT CAGGGATGCC GGAGCCGACC TCAATAAACC     780

GGAGCCTACG TGTGGCCGGA CCCCTCTGCA CCTGGCAGTA GAAGCCCAGG CAGCCAGCGT     840

GCTGGAACTT CTCCTGAAAG CCGGTGCTGA CCCCACCGCC CGCATGTATG GGGCCGCAC     900

CCCGCTTGGC AGTGCCCTGC TCCGGCCCAA CCCCATCCTT GCCCGCCTCC TCCGTGCACA     960

TGGGGCCCCT GAACCTGAGG ACGAGGACGA TAAGCTTAGC CCTTGCAGCA GCAGCGGCAG    1020

CGACAGTGAC AGTGACAACA GAGATGAGGG CGATGAATAT GATGACATCG TGGTTCACAG    1080

TGGCAGGAGC CAAAACCGAC AACCGCCTTC CCCGGCATCC AAACCTCTTC CTGATGACCC    1140

CAACCCTGCC TGACTTAAGT GCTAATATTA ATATAATTTC CAACTTAATA AAATTGCAGA    1200

CCTGACAACC AG                                                       1212

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:5:

Cys Asp Ser Gly Leu Asp Ser Met
1               5

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:6:

Cys Asp Asp Arg His Asp Ser Gly Leu Asp Ser Met
1               5                   10

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:7:
```

```
Cys Asp Asp Arg His Asp Ser Gly Leu Asp Ser Met Lys Asp Glu Glu
1               5                  10                  15
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:8:

```
Cys Glu Arg Leu Leu Asp Asp Arg His Asp Ser Gly Leu Asp Ser Met
1               5                  10                  15

Lys Asp Glu Glu
          20
```

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:9:

```
Cys Lys Lys Glu Arg Leu Leu Asp Asp Arg His Asp Ser Gly Leu Asp
1               5                  10                  15

Ser Met Lys Asp Glu Glu
              20
```

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:10:

```
Ile Gly Arg Arg Gly Lys Val Glu Gln Leu Ser Pro Glu Glu Glu
1               5                  10                  15

Lys Arg Arg
```

(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:11:

```
Cys Lys Lys Glu Arg Leu Leu Asp Asp Arg His Asp Ala Gly Leu Asp
1               5                  10                  15

Ala Met Lys Asp Glu Glu
              20
```

(2) INFORMATION FOR SEQ ID NO:12:

(i) SEQUENCE CHARACTERISTICS:
        (A) LENGTH: 347 amino acids
        (B) TYPE: amino acid
        (C) STRANDEDNESS:
        (D) TOPOLOGY: linear (xi) SEQUENCE DESCRIPTION: SEQ ID NO:12:

```
Met Tyr Pro Tyr Asp Val Pro Asp Tyr Ala Met Tyr Pro Tyr Asp Val
1               5                   10                  15

Pro Asp Tyr Ala Met Tyr Pro Tyr Asp Val Pro Asp Tyr Ala Met Phe
                20                  25                  30

Gln Ala Ala Glu Arg Pro Gln Glu Trp Ala Met Glu Gly Pro Arg Asp
            35                  40                  45

Gly Leu Lys Lys Glu Arg Leu Leu Asp Asp Arg His Asp Ser Gly Leu
        50                  55                  60

Asp Ser Met Lys Asp Glu Glu Tyr Glu Gln Met Val Lys Glu Leu Gln
65                  70                  75                  80

Glu Ile Arg Leu Glu Pro Gln Glu Val Pro Arg Gly Ser Glu Pro Trp
                85                  90                  95

Lys Gln Gln Leu Thr Glu Asp Gly Asp Ser Phe Leu His Leu Ala Ile
                100                 105                 110

Ile His Glu Glu Lys Ala Leu Thr Met Glu Val Ile Arg Gln Val Lys
            115                 120                 125

Gly Asp Leu Ala Phe Leu Asn Phe Gln Asn Asn Leu Gln Gln Thr Pro
        130                 135                 140

Leu His Leu Ala Val Ile Thr Asn Gln Pro Glu Ile Ala Glu Ala Leu
145                 150                 155                 160

Leu Gly Ala Gly Cys Asp Pro Glu Leu Arg Asp Phe Arg Gly Asn Thr
                165                 170                 175

Pro Leu His Leu Ala Cys Glu Gln Gly Cys Leu Ala Ser Val Gly Val
                180                 185                 190

Leu Thr Gln Ser Cys Thr Thr Pro His Leu His Ser Ile Leu Lys Ala
        195                 200                 205

Thr Asn Tyr Asn Gly His Thr Cys Leu His Leu Ala Ser Ile His Gly
210                 215                 220

Tyr Leu Gly Ile Val Glu Leu Leu Val Ser Leu Gly Ala Asp Val Asn
225                 230                 235                 240

Ala Gln Glu Pro Cys Asn Gly Arg Thr Ala Leu His Leu Ala Val Asp
                245                 250                 255

Leu Gln Asn Pro Asp Leu Val Ser Leu Leu Lys Cys Gly Ala Asp
                260                 265                 270

Val Asn Arg Val Thr Tyr Gln Gly Tyr Ser Pro Tyr Gln Leu Thr Trp
        275                 280                 285

Gly Arg Pro Ser Thr Arg Ile Gln Gln Gln Leu Gly Gln Leu Thr Leu
        290                 295                 300

Glu Asn Leu Gln Met Leu Pro Glu Ser Glu Asp Glu Glu Ser Tyr Asp
305                 310                 315                 320

Thr Glu Ser Glu Phe Thr Glu Phe Thr Glu Asp Glu Leu Pro Tyr Asp
                325                 330                 335

Asp Cys Val Phe Gly Gly Gln Arg Leu Thr Leu
                340                 345
```

(2) INFORMATION FOR SEQ ID NO:13:

(i) SEQUENCE CHARACTERISTICS:
        (A) LENGTH: 347 amino acids
        (B) TYPE: amino acid
        (C) STRANDEDNESS:
        (D) TOPOLOGY: linear (xi) SEQUENCE DESCRIPTION: SEQ ID NO:13:

Met Tyr Pro Tyr Asp Val Pro Asp Tyr Ala Met Tyr Pro Tyr Asp Val

```
                        1               5                      10                     15
                    Pro Asp Tyr Ala Met Tyr Pro Tyr Asp Val Pro Asp Tyr Ala Met Phe
                                    20                  25                  30

Gln Ala Ala Glu Arg Pro Gln Glu Trp Ala Met Glu Gly Pro Arg Asp
                                35                  40                  45

Gly Leu Lys Lys Glu Arg Leu Leu Asp Asp Arg His Asp Ala Gly Leu
                        50                  55                  60

Asp Ala Met Lys Asp Glu Glu Tyr Glu Gln Met Val Lys Glu Leu Gln
                    65                  70                  75                  80

Glu Ile Arg Leu Glu Pro Gln Glu Val Pro Arg Gly Ser Glu Pro Trp
                                    85                  90                  95

Lys Gln Gln Leu Thr Glu Asp Gly Asp Ser Phe Leu His Leu Ala Ile
                                100                 105                 110

Ile His Glu Glu Lys Ala Leu Thr Met Glu Val Ile Arg Gln Val Lys
                                115                 120                 125

Gly Asp Leu Ala Phe Leu Asn Phe Gln Asn Asn Leu Gln Gln Thr Pro
                            130                 135                 140

Leu His Leu Ala Val Ile Thr Asn Gln Pro Glu Ile Ala Glu Ala Leu
                    145                 150                 155                 160

Leu Gly Ala Gly Cys Asp Pro Glu Leu Arg Asp Phe Arg Gly Asn Thr
                                    165                 170                 175

Pro Leu His Leu Ala Cys Glu Gln Gly Cys Leu Ala Ser Val Gly Val
                                    180                 185                 190

Leu Thr Gln Ser Cys Thr Thr Pro His Leu His Ser Ile Leu Lys Ala
                                195                 200                 205

Thr Asn Tyr Asn Gly His Thr Cys Leu His Leu Ala Ser Ile His Gly
                            210                 215                 220

Tyr Leu Gly Ile Val Glu Leu Leu Val Ser Leu Gly Ala Asp Val Asn
                    225                 230                 235                 240

Ala Gln Glu Pro Cys Asn Gly Arg Thr Ala Leu His Leu Ala Val Asp
                                    245                 250                 255

Leu Gln Asn Pro Asp Leu Val Ser Leu Leu Leu Lys Cys Gly Ala Asp
                                    260                 265                 270

Val Asn Arg Val Thr Tyr Gln Gly Tyr Ser Pro Tyr Gln Leu Thr Trp
                                275                 280                 285

Gly Arg Pro Ser Thr Arg Ile Gln Gln Gln Leu Gly Gln Leu Thr Leu
                            290                 295                 300

Glu Asn Leu Gln Met Leu Pro Glu Ser Glu Asp Glu Ser Tyr Asp
                    305                 310                 315                 320

Thr Glu Ser Glu Phe Thr Glu Phe Thr Glu Asp Glu Leu Pro Tyr Asp
                                    325                 330                 335

Asp Cys Val Phe Gly Gly Gln Arg Leu Thr Leu
                                    340                 345

(2) INFORMATION FOR SEQ ID NO:14:

(i) SEQUENCE CHARACTERISTICS:
        (A) LENGTH: 389 amino acids
        (B) TYPE: amino acid
        (C) STRANDEDNESS:
        (D) TOPOLOGY: linear (xi) SEQUENCE DESCRIPTION: SEQ ID NO:14:

Met Tyr Pro Tyr Asp Val Pro Asp Tyr Ala Met Tyr Pro Tyr Asp Val
1               5                   10                  15

Pro Asp Tyr Ala Met Tyr Pro Tyr Asp Val Pro Asp Tyr Ala Met Ala
```

```
                    20                  25                  30
Gly Val Ala Cys Leu Gly Lys Thr Ala Asp Ala Asp Glu Trp Cys Asp
        35                  40                  45
Ser Gly Leu Gly Ser Leu Gly Pro Asp Ala Ala Pro Gly Gly Pro
    50                  55                  60
Gly Leu Gly Ala Glu Leu Gly Pro Glu Leu Ser Trp Ala Pro Leu Val
65                  70                  75                  80
Phe Gly Tyr Val Thr Glu Asp Gly Asp Thr Ala Leu His Leu Ala Val
                85                  90                  95
Ile His Gln His Glu Pro Phe Leu Asp Phe Leu Leu Gly Phe Ser Ala
            100                 105                 110
Gly His Glu Tyr Leu Asp Leu Gln Asn Asp Leu Gly Gln Thr Ala Leu
            115                 120                 125
His Leu Ala Ala Ile Leu Gly Glu Ala Ser Thr Val Glu Lys Leu Tyr
    130                 135                 140
Ala Ala Gly Ala Gly Val Leu Val Ala Glu Arg Gly Gly His Thr Ala
145                 150                 155                 160
Leu His Leu Ala Cys Arg Val Arg Ala His Thr Cys Ala Cys Val Leu
                165                 170                 175
Leu Gln Pro Arg Pro Ser His Pro Arg Asp Ala Ser Asp Thr Tyr Leu
            180                 185                 190
Thr Gln Ser Gln Asp Cys Thr Pro Asp Thr Ser His Ala Pro Ala Ala
            195                 200                 205
Val Asp Ser Gln Pro Asn Pro Glu Asn Glu Glu Glu Pro Arg Asp Glu
        210                 215                 220
Asp Trp Arg Leu Gln Leu Glu Ala Glu Asn Tyr Asp Gly His Thr Pro
225                 230                 235                 240
Leu His Val Ala Val Ile His Lys Asp Ala Glu Met Val Arg Leu Leu
                245                 250                 255
Arg Asp Ala Gly Ala Asp Leu Asn Lys Pro Glu Pro Thr Cys Gly Arg
            260                 265                 270
Thr Pro Leu His Leu Ala Val Glu Ala Gln Ala Ala Ser Val Leu Glu
            275                 280                 285
Leu Leu Leu Lys Ala Gly Ala Asp Pro Thr Ala Arg Met Tyr Gly Gly
        290                 295                 300
Arg Thr Pro Leu Gly Ser Ala Leu Leu Arg Pro Asn Pro Ile Leu Ala
305                 310                 315                 320
Arg Leu Leu Arg Ala His Gly Ala Pro Glu Pro Glu Asp Glu Asp Asp
            325                 330                 335
Lys Leu Ser Pro Cys Ser Ser Ser Gly Ser Asp Ser Asp Ser Asp Asn
            340                 345                 350
Arg Asp Glu Gly Asp Glu Tyr Asp Asp Ile Val Val His Ser Gly Arg
        355                 360                 365
Ser Gln Asn Arg Gln Pro Pro Ser Pro Ala Ser Lys Pro Leu Pro Asp
    370                 375                 380
Asp Pro Asn Pro Ala
385
```

COMPOSITIONS AND METHODS FOR MODULATING CELLULAR NF-κB ACTIVATION

TECHNICAL FIELD

The present invention relates generally to compositions and methods for modulating the activation of nuclear factor κB (NF-κB). The invention is more particularly related to agents that modulate ubiquitination of phosphorylated IκBα and/or IκBβ, to methods for identifying such agents and to methods for treating diseases associated with NF-κB activation. Modulating agents encompassed by the present invention include peptides that comprise a recognition domain for E3 ubiquitin ligase.

BACKGROUND OF THE INVENTION

NF-κB is a transcription factor that plays a pivotal role in the highly specific pattern of gene expression observed for immune, inflammatory and acute phase response genes, including interleukin 1, interleukin 8, tumor necrosis factor and certain cell adhesion molecules. Like other members of the Rel family of transcriptional activators, NF-κB is sequestered in an inactive form in the cytoplasm of most cell types. A variety of extracellular stimuli including mitogens, cytokines, antigens, stress inducing agents, UV light and viral proteins initiate a signal transduction pathway that ultimately leads to NF-κB release and activation.

Important modulators of NF-κB activation are the inhibitor proteins IκBα and IκBβ (referred to herein as IκB), which associate with (and thereby inactivate) NF-κB in vivo. Activation and nuclear translocation of NF-κB occurs following signal-induced phosphorylation of IκB, which leads to proteolysis via the ubiquitin pathway. For IκBα, the stimulus-induced phosphorylation at serines 32 and 36 renders the inhibitor a target for ubiquitination at lysines 21 and 22, resulting in degradation. Similarly, phosphorylation of IκBβ at serines 19 and 23 renders the inhibitor a target for ubiquitination at lysine 9. However, neither the site at which IκBs are recognized by the ubiquitin system, nor the component(s) of the ubiquitin system mediating IκB recognition have been identified.

Degradation of a protein via the ubiquitin pathway proceeds by two discrete and successive steps: (a) covalent attachment of multiple ubiquitin molecules to the protein substrate, and (b) degradation of the targeted protein by the 26S proteasome complex. The ubiquitin pathway consists of several components that act in concert and in a hierarchical manner (for reviews, see Ciechanover, *Cell* 79:13, 1994; Hochstrasser, *Curr. Op. Cell. Biol.* 7:215, 1995; Jentsch and Schlenker, *Cell* 82:881, 1995; Deshaies, *Trends Cell Biol.* 5:428, 1995). One such component, a single E1 enzyme, carries out activation of ubiquitin. Several major species of E2 enzymes have been characterized in mammalian cells, plants, and yeast. E2 enzymes probably bind to the ligase E3 (Reiss and Hersko, *J. Biol. Chem.* 265:3685, 1990; Dohmen et al., *Proc. Natl. Acad. Sci. USA* 88:7351, 1991) and it appears that each E2 enzyme can act with one or more E3 proteins (Nuber et al., *J. Biol. Chem.* 271:2795, 1996; Orian et al., *J. Biol. Chem.* 270:21707,1995; Stancovski et al., *Mol. Cell. Biol.* 15:7106, 1995; Gonen et al., *J. Biol. Chem.* 271:302,1996).

Only few E3 enzymes (ubiquitin ligases) have been described. Mammalian E3α (UBR1 in yeast) and E3β recognize protein substrates via their free N-terminal amino acid residues ("N-end rule"; Varshavsky, *Cell* 69:725, 1992; Hershko and Ciechanover, *Ann. Rev. Biochem.* 61:761, 1992). Cdc53 is probably an E3 involved in targeting phosphorylated G1 cyclins (Willems et al., *Cell* 86:453, 1996). E6-AP is involved in recognition of p53 (Scheffner et al., *Cell* 75:495, 1993), and a series of unique E6-AP homologous proteins have been identified (Huibregtse et al., *Proc. Natl. Acad. Sci. USA* 92:2563, 1995): Nedd4 is involved the degradation of the epithelial $Na^+$ channel (Staub et al, *Embo J* 15:2371, 1996) and RSP5 (NIP1) is involved in tagging the permeases Gap1 and Fur1 (Hein et al., *Mol. Microbiol.* 18:77, 1995), whereas Pub1 targets Cdc25 (Nefsky and Beach, *EMBO J* 15:1301, 1996). Several other E3 enzymes that have been recently isolated appear to be involved in the degradation of c-Fos, a subset of muscle proteins, and in the processing of p105, the NF-κB precursor (Orian et al., *J Biol. Chem.* 270:21707, 1995; Stancovski et al., *Mol. Cell. Biol.* 15:7106, 1995; Gonen et al., *J Biol. Chem.* 271:302,1996). Thus, it appears that the ligases represent a large, mostly unraveled family of enzymes and, except for the mode of recognition of the "N-end rule" ligases (E3α and E3β), the recognition motifs of all other known substrates of the ubiquitin system have not been identified.

Accordingly, there is a need in the art for an improved understanding of IκB degradation via the ubiquitin pathway, and for the identification of modulators of this degradation process for use in treating diseases associated with activation of NF-κB. The present invention fulfills these needs and further provides other related advantages.

SUMMARY OF THE INVENTION

Briefly stated, the present invention provides compositions and methods for modulating the activation of nuclear factor κB (NF-κB) by modulating ubiquitination of phosphorylated IκBα and/or IκBβ. Within one aspect, the present invention provides a method for assaying the ability of an IκB polypeptide to undergo ubiquitination in vivo, comprising: (a) incubating an IκB polypeptide with a cellular extract, wherein the step of incubating is carried out under conditions and for a time sufficient to allow phosphorylation of the IκB polypeptide and formation of a complex comprising phosphorylated IκB polypeptide and NF-κB; (b) subsequently subjecting the complex to in vitro ubiquitination; and (c) subsequently evaluating the extent of ubiquitination of the complex, and thereby assaying the ability of the IκB polypeptide to undergo ubiquitination in vivo.

Within another aspect, a method for identifying an agent that modulates ubiquitination of IκBα and/or IκBβ is provided, comprising: (a) incubating a candidate agent with an IκB polypeptide and a cellular extract, wherein the step of incubating is carried out under conditions and for a time sufficient to allow phosphorylation of the IκB polypeptide and formation of a complex comprising phosphorylated IκB polypeptide and NF-κB; and (b) subsequently measuring the ability of the candidate agent to modulate ubiquitination of the complex, and therefrom identifying an agent that modulates ubiquitination of IκBα and/or IκBβ.

The present invention also provides agents that modulate ubiquitination of IκBα and/or IκBβ. Such agents include peptides that comprise a recognition domain or E3 ubiquitin ligase including, for example, the peptides recited in SEQ ID NO:5–SEQ ID NO:9. Isolated DNA molecules and recombinant expression vectors encoding peptide agents, as well as host cells transformed or transfected with such an expression vector, are also provided.

Within another aspect, the present invention provides pharmaceutical compositions comprising one or more agents that modulate ubiquitination of IκBα and/or IκBβ in combination with a pharmaceutically acceptable carrier.

The present invention also provides, within further aspects, methods for modulating NF-κB activity in a patient and for treating a patient afflicted with a disorder associated with NF-κB activation, comprising administering to a patient a pharmaceutical composition as described above. Disorders associated with NF-κB activation include inflammatory diseases, autoimmune diseases, cancer and viral infection.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 1A, lane 1 shows the ubiquitination of an IκBα polypeptide that contains alanine residues at positions 32 and 36 (S32/36A; SEQ ID NO:13) and lane 2 shows the ubiquitination of a non-phosphorylated wild-type IκBα polypeptide (SEQ ID NO:12). In lanes 3–14, the ubiquitination substrate was wild-type IκBα (SEQ ID NO: 12). In lane 3, ubiquitination was performed in the absence of ATP; and in lanes 4–14 the reaction was performed in the presence of ATPγS with (lanes 5–14) or without (lane 4) a candidate peptide modulating agent. The candidate agents shown are: 400 μM c-Fos phosphopeptide (ppFos (SEQ ID NO:10), lane 5); 400 μM serine 32, 36 to alanine substituted IκBα peptide (pp21S/A (SEQ ID NO:11), lane 6); 40 μM doubly phosphorylated IκBα peptide (pp21 (SEQ ID NO:9), lane 7); 400 μM non-phosphorylated IκBα peptide (p21 (SEQ ID NO:9), lane 8); 100 μM singly phosphorylated IκBα peptides (ppS32 (SEQ ID NO:9), lane 9; ppS36 (SEQ ID NO:9), lane 10); and 40 μM shorter, doubly phosphorylated IκBα peptides (pp19 (SEQ ID NO:8), lane 11; pp15 (SEQ ID NO:7), lane 12; pp11 (SEQ ID NO:6), lane 13; pp7 (SEQ ID NO:5), lane 14).

In FIG. 1B, the ubiquitination substrate was free wild type IκBα (SEQ ID NO:12, lanes 1–3) or free S32/36A substituted IκBα (SEQ ID NO:13, lanes 4–6). The reaction was performed in the absence (lanes 1 and 4) or presence (lanes 2, 3, 5 and 6) of ATPγS. 40 μM doubly phosphorylated IκBα peptide (pp21 (SEQ ID NO:9) was added to the conjugation reaction mixture in the samples shown in lanes 3 and 6.

In FIG. 1C, the ubiquitination of bulk cellular proteins in HeLa extract is shown. Lane 1 shows the ubiquitination in the absence of ATP, and lane 5 shows the ubiquitination in the presence of ATP. In lanes 3–5, candidate modulating agents were added: 40 μM doubly phosphorylated IκBα peptide (pp21 (SEQ ID NO:9), lane 2); 400 μM c-Fos phosphopeptide (ppFos (SEQ ID NO:10), lane 3); and 400 μM non-phosphorylated IκBα peptide (p21 (SEQ ID NO:9), lane 4).

In FIG. 1D, the ubiquitination substrate was phosphorylated (lanes 2–7) or non-phosphorylated (lane 1) wild type IκBβ (SEQ ID NO:14). Reactions were performed in the absence (lane 2) or presence (lanes 1, 3–7) of ATγS, and with (lanes 4–7) or without (lanes 1–3) a candidate peptide modulating agent. The candidate agents shown are: 40 μM doubly phosphorylated IκBα peptide (pp21 (SEQ ID NO:9), lane 4); 400 μM c-Fos phosphopeptide (ppFos (SEQ ID NO:10), lane 5); 40 μM doubly phosphorylated IκBα peptide (pp19 (SEQ ID NO:8), lane 6); and 400 μM non-phosphorylated IκBα peptide (p21 (SEQ ID NO:9), lane 7).

In FIGS. 4A–C, pp21 (FIGS. 4A and 4B) or ppFos (FIG. 4C) was microinjected into the cytoplasm of HeLa cells. Cells were then activated immediately with TNFα and immunostained with anti-p65 antibodies. In FIGS. 4D–F, pp21 (FIG. 4D) or ppFos (FIG. 4F) was injected into the cytoplasm of human vascular endothelial cells (HUVEC). Cells were then activated immediately with TNFα and immunostained with anti-E-selectin antibodies. FIG. 4E is a phase contrast photograph of FIG. 4D. In each micrograph, the injected cells are marked by large arrows. A non-injected, E-selectin negative cell is marked by a small arrow in FIGS. 4D and 4E.

In FIG. 4G, the percent of HeLa cells displaying nuclear p65 staining is shown. 90 and 42 cells were microinjected with pp21 and ppFos, respectively. FIG. 4H shows the percent of HUVEC displaying E-selectin staining. 160 and 36 cells were microinjected with pp21 and ppFos, respectively. For each graph, column 1 shows the level in the absence of candidate modulating agent and TNFα activation. Columns 2–4 show the level following TNFα activation in the absence of candidate modulating agent (column 2) or in the presence of pp21 (column 3) or ppFos (column 4).

DETAILED DESCRIPTION OF THE INVENTION

Figure 1A:
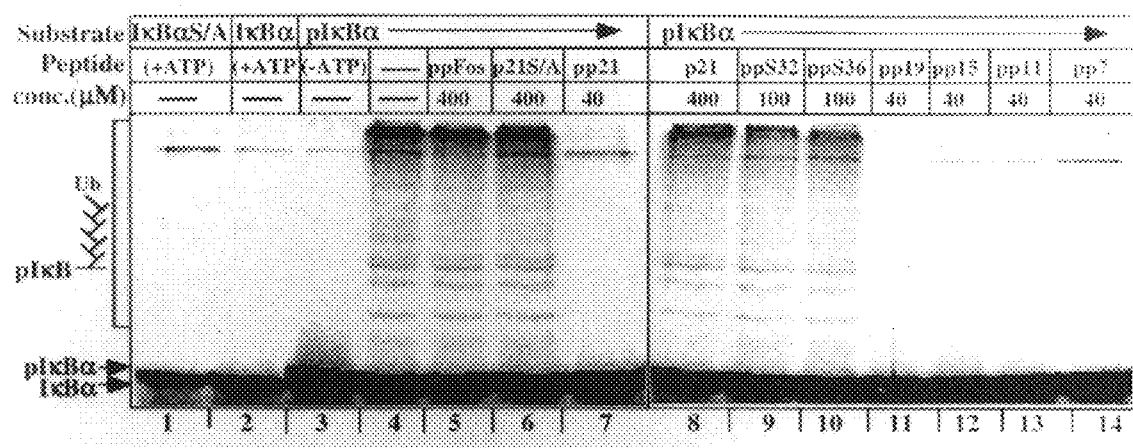
FIGS. 1A–1D are autoradiograms depicting the results of SDS-PAGE analysis of ubiquitination assays performed in the presence and absence of representative modulating agents. Unless otherwise indicated, the substrate was an $^{35}$S-labelled, HA-tagged IκB polypeptide that was phosphorylated and NF-κB complex-associated.

As noted above, the present invention is generally directed to compositions and methods useful for modulating the activation of nuclear factor κB (NF-κB) and for treating diseases associated with such activation. In particular, the invention is directed to agents that modulate ubiquitination of phosphorylated IκB (i.e., IκBα and/or IκBβ), and to methods for identifying such agents.

In response to a stimulus, IκB associated with NF-κB is activated (i.e., phosphorylated), rendering IκB a target for degradation and thereby releasing and activating NF-κB. It has been found, within the context of the present invention, that phosphorylated and NF-κB-associated IκB is recognized by a specific ubiquitin ligase, E3. The N-terminal signal-induced phosphorylation site that is functionally conserved between IκBα and IκBβ constitutes the E3 recognition motif and is distinct from the nearby ubiquitination site. Peptides corresponding to this motif, and variants thereof, inhibit the ubiquitination of IκB and its subsequent degradation, and such peptides are modulating agents within the scope of the present invention.

Within one aspect, the present invention provides an in vitro ubiquitination assay that reproduces the in vivo ubiquitination of IκBα with high fidelity. In vivo, IκB is targeted for degradation by phosphorylation at serines 32 and 36, while altered forms of IκBα that contain alanine residues at positions 32 and 36 are not subject to ubiquitin conjugation. Similarly, phosphorylation at serines 19 and 23 is required for ubiquitination of IκBβ. However, free IκB is recognized by the ubiquitin system in a non-discriminatory manner (i.e., phosphorylation is not required). The ubiquitination assay provided herein allows regulation of IκB ubiquitination that corresponds to the regulation observed in vivo.

IκB polypeptides for use in a ubiquitination assay as described herein may be native human IκBα (SEQ ID NO:1) or IκBβ (SEQ ID NO:3), or may be a variant of a native protein. As used herein, a variant is a polypeptide that contains one or more substitutions and/or modifications. Variants include truncated polypeptides and polypeptides containing additional amino acid sequences that have minimal influence on the activity of the polypeptide. In particular, variants may contain additional amino acid sequences at the amino and/or carboxy termini. Such sequences may be used, for example, to facilitate purification or detection of the polypeptide. Polypeptide variants of IκB are modified such that the ability of the variant to be phosphorylated and ubiquitinated within a ubiquitination assay as described herein is not substantially diminished. Preferably, the IκB polypeptide is labeled. For example, $^{35}$S may be incorporated into a IκB polypeptide by in vitro translation of the polypeptide in the presence of $^{35}$-methionine, using standard techniques.

An IκB polypeptide may generally be prepared from DNA encoding the polypeptide by expression of the DNA in cultured host cells or by translation using an in vitro system such as wheat germ extract. If host cells are employed, such cells are preferably are bacteria, yeast, baculovirus-infected insect cells or mammalian cells. The recombinant DNA may be cloned into any expression vector suitable for use within the host cell, using techniques well known to those of ordinary skill in the art. In vitro translation of polypeptide may generally be performed according to the manufacturer's instructions.

The DNA sequences expressed in this manner may encode native IκBα or IκBβ, or may encode portions or variants of a native IκB. DNA molecules encoding variants may generally be prepared using standard mutagenesis techniques, such as oligonucleotide-directed site-specific mutagenesis. Sections of the DNA sequence may also, or alternatively, be removed to permit preparation of truncated polypeptides and DNA encoding additional sequences such as "tags" may be added to the 5' or 3' end of the DNA molecule. For example, DNA encoding an IκB polypeptide may also encode an epitope, such that the recombinant protein contains the epitope at the N- or C-terminus. Epitopes such as glutathione-S transferase protein (GST), HA (hemaglutinin)-tag, FLAG and Histidine-tag may be added using techniques well known to those of ordinary skill in the art.

Expressed IκB polypeptides may be used without purification following in vitro translation. Alternatively, a polypeptide may be isolated in substantially pure form. An IκB polypeptide may be isolated to a purity of at least 80% by weight, preferably to a purity of at least 95% by weight, and more preferably to a purity of at least 99% by weight. In general, such purification may be achieved using, for example, the representative purification method described herein or the standard techniques of ammonium sulfate fractionation, SDS-PAGE electrophoresis, and affinity chromatography.

Within a ubiquitination assay as provided herein, cellular extracts from stimulated or non-stimulated Jurkat, HeLa, THP-1 or endothelial cells are incubated in vitro with an IκB polypeptide in the presence of ATP and the phosphatase inhibitor okadaic acid. Cellular extracts may generally be prepared according to the method of Alkalay et al., *Proc. Natl. Acad Sci. USA* 92:10599, 1995. The incubation is performed under conditions sufficient to result in phosphorylation of the IκB polypeptide (at serines 32 and 36 for IκBα and variants thereof) and association of the phosphorylated polypeptide (pIκB) with the cellular-derived NF-κB complex. For example, IκB polypeptide may be incubated with HeLa or Jurkat cell extract, ATP and okadaic acid. Incubation for 90 minutes at 30° C. is generally sufficient to allow phosphorylation of the IκB polypeptide. Following this incubation, the pIκB/NF-κB complex may be immunopurified with, for example, anti-p65 antibodies and subjected to in vitro ubiquitination in a cell free system, as described by Alkalay et al., *Proc. Natl. Acad Sci. USA* 92:10599, 1995. The level of ubiquitination may then be evaluated using the well known techniques of SDS-PAGE, followed by autoradiography.

Figure 1B:
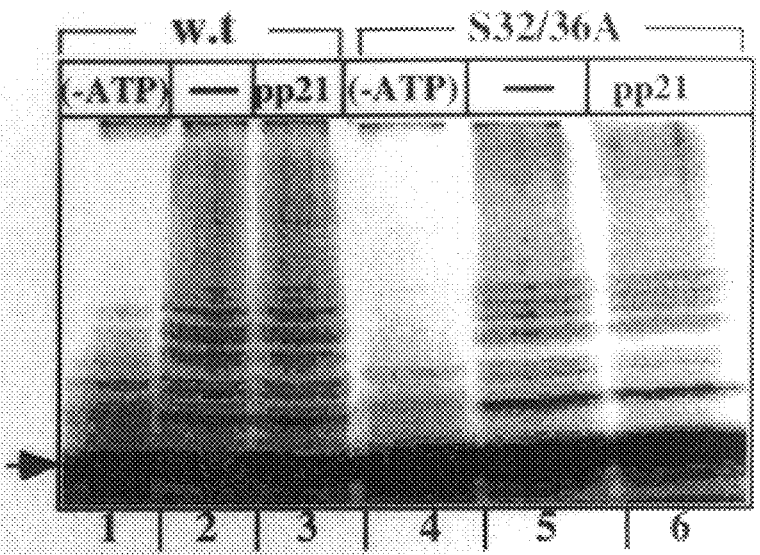

Under these conditions, a wild type $^{35}$S-pIκBα polypeptide generates multiply ubiquitinated species in the presence of ATPγS (see FIG. 1A, lane 4). Neither $^{35}$S-labeled S32/36A mutant of IκBα (lane 1), nor the non-phosphorylated wild type $^{35}$S-IκBα (lane 2) are ubiquitinated. However, free forms of either mutant or wild type IκBα are readily conjugated (FIG. 1B). Similarly, a free (but not a complex-associated) lysine 21, 22 mutant of IκBα can be ubiquitinated in vitro. Thus, unlike ubiquitination assays performed using free IκB polypeptides, the ubiquitination assay provided herein targets only IκB polypeptides that are complex-associated and appropriately phosphorylated.

In another aspect of the present invention, a ubiquitination assay as described above may be used to identify agents that modulate ubiquitination of IκB. Modulating agents may include antibodies (e.g., monoclonal), peptides and other drugs that stimulate or, preferably, inhibit ubiquitination of an IκBα and/or IκBβ polypeptide. In general, such agents may be identified by including a candidate modulating agent in the ubiquitination reaction, which may otherwise be performed as described above, and evaluating the effect of the agent on the level of ubiquitination. A suitable concentration of candidate agent for use in such an assay generally ranges from about 0.1 μM to about 1 mM. For peptide candidate agents, a peptidase inhibitor such as Bestatin (40 μg/mL) may also be added, and the amount of peptide preferably ranges from about 10 μM to about 1 mM. A candidate agent that results in a statistically significant effect on the level of ubiquitination is a modulating agent encompassed by the present invention.

As noted above, it has been found, within the context of the present invention, that complex-associated IκB is recognized by a specific ubiquitin ligase, E3. Accordingly, modulating agents within the scope of the present invention include, but are not limited to, peptides that comprise a recognition domain for E3 ubiquitin ligase. Such peptides may be derived from the N-terminal signaling domain (residues 1 to 54 of native IκBα or IκBβ) and, at minimum, should contain the signaling phosphorylation site (residues 32 to 36 of native IκBα or residues 19 to 23 of native IκBβ). Peptide modulating agents may generally be prepared using standard automated synthesis techniques or by expression of recombinant DNA encoding the desired peptide. Such agents may differ in sequence from native IκBα and IκBβ, due to one or more substitutions and/or modifications, as described above, provided that the peptide variant inhibits ubiquitination of an IκB polypeptide.

For maximal inhibition, peptide modulating agents should be phosphorylated; preferably at both of the native phosphorylation sites (e.g., serines 32 and 36 of IκBα), although singly phosphorylated peptides may be employed. Phosphorylated peptides may be prepared using well known techniques. For example phosphoserine residues may be incorporated into a peptide during synthesis. Alternatively, a peptide may be phosphorylated using standard techniques following synthesis.

In general, peptide modulating agents may be prepared using standard techniques, incorporating amino acids and/or amino acid analogs. During synthesis, active groups of amino acids and/or amino acid analogs may be protected as necessary using, for example, a t-butyldicarbonate (t-BOC) group or a fluorenylmethoxy carbonyl (FMOC) group. Amino acids and amino acid analogs may be purchased commercially (e.g., Sigma Chemical Co.; Advanced Chemtec) or synthesized using methods known in the art. Peptides may be synthesized using a solid phase method, in which the peptides are attached to a resin such as 4-methylbenzhydrylamine (MBHA), 4-(oxymethyl)-phenylacetamido methyl- and 4-(hydroxymethyl)phenoxy methyl-copoly(styrene-1% divinylbenzene) (Wang resin), all of which are commercially available, or to p-nitrobenzophenone oxime polymer (oxime resin) which can be synthesized as described by De Grado and Kaiser, *J. Org. Chem.* 47:3258, 1982. Those skilled in the art will realize that the choice of amino acids and/or amino acid analogs will depend, in part, on the specific physical, chemical or biological characteristics desired. Such characteristics are determined, in part, by the method of administration and the target location within a patient.

Selective modification of the reactive groups in a peptide can also impart desirable characteristics. Peptides can be manipulated while still attached to the resin to obtain N-terminal modified compounds such as an acetylated peptide or can be removed from the resin using hydrogen fluoride or an equivalent cleaving agent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus or amidation of the C-terminus. Similarly, methods for modifying side chains of the amino acids or amino acid analogs are well known to those skilled in the art of peptide synthesis. The choice of modifications made to reactive groups present on the peptide will be determined by the desired characteristics.

A modulating agent may also be a cyclic peptide. A cyclic peptide can be obtained by inducing the formation of a covalent bond between, for example, the amino group at the N-terminus of the peptide and the carboxyl group at the C-terminus. Alternatively, a cyclic peptide can be obtained by forming a covalent bond between a terminal reactive group and a reactive amino acid side chain or between two reactive side chains. It will be apparent to those of skill in the art that a cyclic peptide is selected based on the desired properties. For example, a cyclic peptide may provide increased stability, increased solubility, decreased immunogenicity or decreased clearance in vivo.

A newly synthesized peptide can be purified using a method such as reverse phase high performance liquid chromatography (RP-HPLC) or other methods of separation based on size or charge. Furthermore, a purified peptide can be characterized using these and other well known methods such as amino acid analysis and mass spectrometry.

Some representative examples of peptide modulating agents are provided in Table I.

TABLE I

Representative Peptide Modulating Agents

| Peptide | Sequence |
| --- | --- |
| pp7 | CDS*GLDS*M |
| pp11 | CDDRHDS*GLDS*M |
| pp15 | CDDRHDS*GLDS*MKDEE |
| pp19 | CERLLDDRHDS*GLDS*MKDEE |
| pp21 | CKKERLLDDRHDS*GLDS*MKDEE |

*indicates phosphorylated residue

Further characterization of modulating agents may be achieved using a ubiquitin-dependent in vitro degradation assay. Such an assay may generally be performed as described by Alkalay et al., *Proc. Natl. Acad. Sci. USA* 92:10599, 1995. Within this assay, pIκBα from stimulated cells is degraded in vitro in a ubiquitin-dependent manner, whereas non-phosphorylated IκBα from the same cell extract is not subject to degradation. Modulating agents that inhibit ubiquitination of IκBα should also result in stabilization of pIκBα within such an in vitro degradation assay.

Modulating agents as described herein may generally be used to specifically inhibit cellular NF-κB functions. Such inhibition may generally be demonstrated by microinjection of the agent (e.g., about 5 mg/mL of a peptide agent) into a suitable cell (e.g., HeLa cell or primary human vascular endothelial cell). Following microinjection, cells are stimulated (e.g., with TNFα) and incubated to allow NF-κB activation. In HeLa cells, TNFα induces rapid nuclear translocation of NF-κB into the nucleus, which may be detected by staining with p65-specific antibodies. Modulating agents induce a statistically significant decrease in NF-κB translocation, and may reduce such translocation to undetectable levels.

Primary human vascular endothelial cells (HUVEC) respond to TNFα stimulation by surface expression of NF-κB regulated adhesion proteins such as ICAM-1, V-CAM-1 and E-selectin (Read et al., *Immunity* 2:493,1995; Chen et al., *J. Immunol* 155:3538, 1995). E-selectin expression is particularly NF-κB dependent and is the major inducible endothelial adhesion molecule for initial neutrophil attachment and rolling on activated endothelium. Stimulated cells may be fixed and stained to detect expression of one or more NF-κB regulated adhesion proteins. Microinjection of a modulating agent results in a statistically significant inhibition of such expression, but does not affect the expression of NF-κB independent adhesion proteins, such as ICAM2.

Modulating agents may also be used to modulate ubiquitination of IκBα and/or IκBβ in a patient, thereby modulating NF-κB cellular function in vivo. As used herein, a "patient" may be any mammal, including a human, and may be afflicted with a disease associated with NF-κB activation, or may be free of detectable disease. Accordingly, the treatment may be of an existing disease or may be prophylactic. Diseases associated with NF-κB activation include inflammatory diseases, autoimmune diseases, cancer and viral infection.

Treatment refers to administration of a modulating agent as described herein. For administration to a patient, one or more such compounds are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Alternatively, a pharmaceutical composition may comprise a polynucleotide encoding a modulating agent (such that the modulating agent is generated in situ) in combination with a physiologically acceptable carrier. In such pharmaceutical compositions, the polynucleotide may be present within any of a variety of delivery systems known to those of ordinary skill in the art, including nucleic acid, bacterial and viral expression systems, as well as colloidal dispersion systems, including liposomes. Appropriate nucleic acid expression systems contain the necessary polynucleotide sequences for expression in the patient (such as a suitable promoter and terminating signal). DNA may also be "naked," as described, for example, in Ulmer et al., *Science* 259:1745–1749, 1993.

Various viral vectors that can be used to introduce a nucleic acid sequence into the targeted patient's cells include, but are not limited to, vaccinia or other pox virus, herpes virus, retrovirus, or adenovirus. Techniques for incorporating DNA into such vectors are well known to those of ordinary skill in the art. Preferably, the retroviral vector is a derivative of a murine or avian retrovirus including, but not limited to, Moloney murine leukemia virus (MoMuLV), Harvey murine sarcoma virus (HaMuSV), murine mammary tumor virus (MuMTV), and Rous Sarcoma Virus (RSV). A retroviral vector may additionally transfer or incorporate a gene for a selectable marker (to aid in the identification or selection of transduced cells) and/or a gene that encodes the ligand for a receptor on a specific target cell (to render the vector target specific). For example, retroviral vectors can be made target specific by inserting a nucleotide sequence encoding a sugar, a glycolipid, or a protein. Targeting may also be accomplished using an antibody, by methods known to those of ordinary skill in the art.

Viral vectors are typically non-pathogenic (defective), replication competent viruses, which require assistance in order to produce infectious vector particles. This assistance can be provided, for example, by using helper cell lines that contain plasmids that encode all of the structural genes of the retrovirus under the control of regulatory sequences within the LTR, but that are missing a nucleotide sequence which enables the packaging mechanism to recognize an RNA transcript for encapsulation. Such helper cell lines include (but are not limited to) Ψ2, PA317 and PA12. A retroviral vector introduced into such cells can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques* 6:882, 1988).

The targeting of liposomes can be classified based on anatomical and mechanistic factors. Anatomical classification is based on the level of selectivity and may be, for example, organ-specific, cell-specific, and/or organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

Routes and frequency of administration, as well doses, will vary from patient to patient. In general, the pharmaceutical compositions may be administered intravenously, intraperitoneally, intramuscularly, subcutaneously, intracavity or transdermally. Between 1 and 6 doses may be administered daily. A suitable dose is an amount that is sufficient to show improvement in the symptoms of a patient afflicted with a disease associated with NF-κB activation. Such improvement may be detected by monitoring inflammatory responses (e.g., edema, transplant rejection, hypersensitivity) or through an improvement in clinical symptoms associated with the disease. In general, the amount of modulating agent present in a dose, or produced in situ by DNA present in a dose, ranges from about 1 μg to about 100 mg per kg of host. Suitable dose sizes will vary with the size of the patient, but will typically range from about 10 mL to about 500 mL for 10–60 kg animal.

The following Examples are offered by way of illustration and not by way of limitation.

EXAMPLES

Example 1

Identification of Modulating Agents using Ubiquitination Assay

This Example illustrates a representative ubiquitination assay, and the use of such an assay to evaluate candidate modulating agents.

A. In vitro Ubiquitination Assay

HA-tagged IκBα or HA-tagged IκBβ cDNAs (Haskill et al., Cell 65:1281–1289, 1991) were translated in vitro in wheat germ extract in the presence of $^{35}$S-methionine according to the manufacturer's instructions (Promega, Madison, Wis.). To phosphorylate IκBα or IκBβ, 1 μl of the extract containing the labeled protein was incubated for 90 minutes at 30° C. in a reaction mixture having a final volume of 30 μl: 100 μg HeLa or Jurkat cell extract (prepared as described by Alkalay et al., Proc. Natl. Acad. Sci. USA 92:10599, 1995), 2 mM ATP and 1 μM okadaic acid. During this incubation, the labeled IκB polypeptide was phosphorylated at serines 32 and 36, and associated with the endogenous NF-κB complex (data not shown).

Following incubation, 1 μl of anti-p65 serum was added, and the NF-κB immune complex was immobilized to Protein A-Sepharose® and subjected to in vitro ubiquitination in HeLa cell extract as described by Alkalay et al. Ubiquitinated proteins were separated by SDS-PAGE and visualized by autoradiography.

As shown in FIG. 1A, only wild type $^{35}$S-pIκBα generated multiply ubiquitinated species (lane 4). Neither $^{35}$S-labeled S32/36A mutant of IκBα (lane 1) nor the non-phosphorylated wild type $^{35}$S-IκBα (lane 2) were ubiquitinated, and no ubiquitination of pIκBα was seen in the absence of ATP (lane 3).

The physiological relevance of this assay was further documented by comparison of in vitro ubiquitination of free $^{35}$S-IκB to that of a complex-associated, phosphorylated substrate. Whereas a complex-associated S32/36A mutant was not subject to ubiquitin conjugation in accordance with its in vivo fate, free forms of either mutant or wild type IκBβ were readily conjugated (FIG. 1B). Similarly, only free, but not a complex-associated lysine 21, 22 mutant of IκBα could be ubiquitinated in vitro (data not shown). Thus, while the free IκBα is recognized by the ubiquitin system in a non-discriminatory manner, the complex-associated inhibitor is masked unless it is appropriately phosphorylated.

B. Identification of Peptide Modulating Agents

To identify the IκBα-ubiquitin ligase recognition motif, various peptides were added at varying concentrations to the reaction mixtures in the presence of the peptidase inhibitor Bestatin (40 μg/ml). The peptides spanned the N-terminal signaling domain of the protein, and were phosphorylated at one or both serine residues (32 and 36), or were unmodified or serine-substituted. These peptides were included in the ubiquitination reaction at different concentrations and tested for inhibition of pIκBα specific ubiquitination. When conjugation of free IκBα was monitored, the translated protein was added directly to the conjugation reaction mixture.

Only peptides that were phosphorylated at both serine 32 and 36 (pIκBα peptides) effectively inhibited pIκBα ubiquitination (FIG. 1A, lanes 7, 11–14). A c-Fos phosphopeptide (ppFos, lane 5), a serine 32, 36 to alanine substituted IκBα peptide (p21 S/A, lane 6) and a non-phosphorylated peptide (p21, lane 8) had no detectable effect on the ubiquitination of pIκB at a concentration of 400 μM. The $IC_{50}$ of the phosphorylated IκBα peptides were calculated and representative inhibitory concentrations are shown in FIG. 1A. Doubly phosphorylated IκBα peptides inhibited the pIκB conjugation reaction (lanes 7, 11–14) at an $IC_{50}$ of 5 μM. The sequences of these peptides are provided in Table I, above, and in SEQ ID NOs:5–9. In contrast, singly phosphorylated peptides (lanes 9, 10) inhibited the pIκBα conjugation at an $IC_{50}$ of 400 μM. The minimal size peptide tested (pp7, lane 14), merely spanning the signaling phosphorylation site, was sufficient to effectively inhibit the ubiquitination, although at somewhat higher $IC_{50}$ (10 μM). Thus, a peptide comprising residues 21 to 41 of SEQ ID NO:1 comprises a recognition domain for E3 ubiquitin ligase. Interestingly, lysine residues 21 and 22 are not essential for inhibition, implying that the ubiquitin-system recognition site is distinct from the actual conjugation site.

Figure 1C:
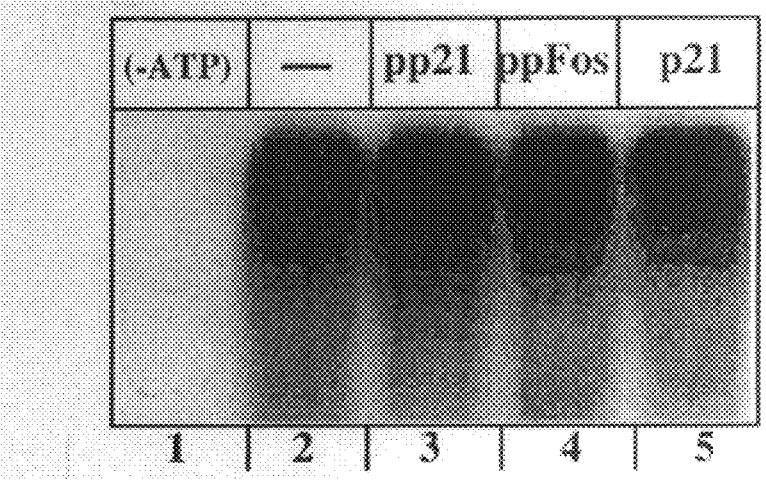

The specificity of the peptide modulating agents was tested in two other ubiquitin-conjugation reactions: the conjugation of free wild type (FIG. 1B lanes 1–3) or S32/36A mutant IκBα (FIG. 1B, lanes 4–6) and the ubiquitin conjugation to the bulk of cellular proteins in HeLa extract (detected by $^{125}$I-labeled ubiquitin according to Alkalay et al., FIG. 1C). Neither reaction was affected by the addition of a peptide modulating agent or a control peptide.

Figure 1D:
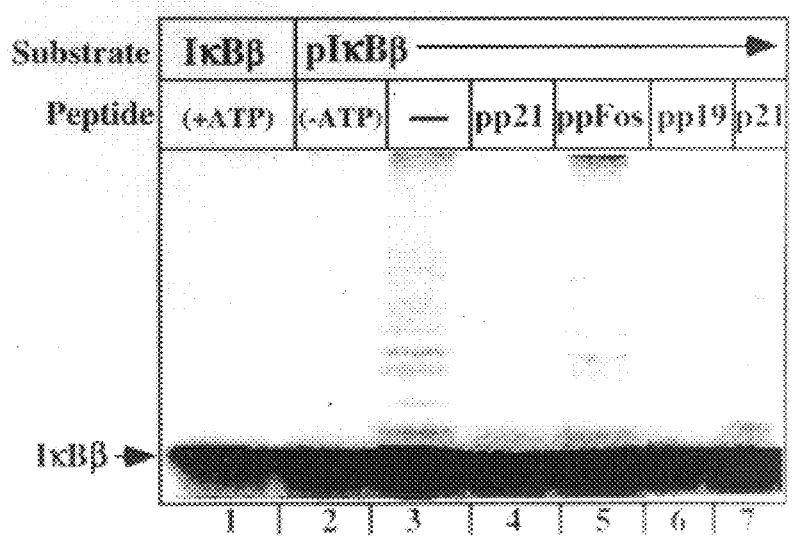

Peptide modulating agents were found to abolish the ubiquitination of the pIκBα related substrate pIκBβ (FIG. 1D). Similar to the conjugation of pIκBα, the specific conjugation of the IκBβ also required an associated NF-κB complex (not shown) and prior phosphorylation at the IκBα-homologous residues Ser 19 and 23. An IκBβ substrate prepared in the absence of phosphatase inhibitors was not subject to ubiquitination (FIG. 1D, lane 1). Peptide modulating agents affected pIκBβ ubiquitination at an $IC_{50}$ that was similar to that observed for pIκBα (FIG. 1D, lanes 4–7). Hence, it appears that the same enzyme(s) target both IκBs for ubiquitin-dependent degradation.

Figure 2:
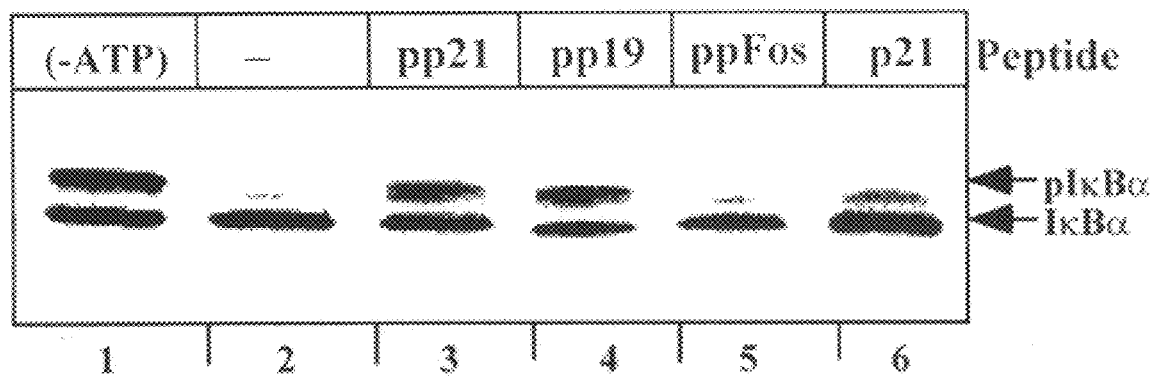
FIG. 2 is an autoradiogram depicting the results of an in vitro ubiquitin-dependent degradation assay performed using extracts from stimulated HeLa cells. In each lane of the SDS-PAGE, the level of phosphorylated (upper band) and non-phosphorylated (lower band) HA-tagged IκBα polypeptide (SEQ ID NO: 12) following the degradation assay is shown. Lane 1 shows the level of these polypeptides following a degradation assay performed without ATP. In lanes 2–6, ATP was included in the reaction mixture. 40 μM candidate modulating agents were added to the reactions shown in lanes 3–6: doubly phosphorylated IκBα peptide (pp21 (SEQ ID NO:9), lane 3); doubly phosphorylated IκBα peptide (pp19 (SEQ ID NO:8), lane 4); c-Fos phosphopeptide (ppFos (SEQ ID NO:10), lane 5); and non-phosphorylated IκBα peptide (p21 (SEQ ID NO:9), lane 6).

The inhibitory pIκBα peptides were tested in a complementary ubiquitin-dependent in vitro degradation assay (Orian et al., J Biol. Chem. 270:21707, 1995; Stancovski et al., Mol. Cell. Biol. 15:7106, 1995). Using this assay, only pIκBα derived from stimulated cells is degraded in vitro in a ubiquitin-dependent manner, whereas the non-phosphorylated IκBα from the same cell extract is not subject to degradation. Incorporation of the conjugation-inhibitory phosphopeptide modulating agents into the degradation assay resulted in stabilization of the pIκBα substrate (FIG. 2, lanes 3, 4) whereas the non-phosphorylated peptide agent or a control phospho-Fos peptide had no effect on the specific pIκBα degradation (lanes 5, 6). Trimming the peptides at Lys 21/22 did not diminish the degradation inhibitory effect (lane 4), indicating that the peptides do not abolish pIκBα degradation by exhausting the ubiquitin-proteasome system as conjugatable substrates.

Example 2

Identification of Ubiquitin System Component Involved in Substrate Recognition

This Example illustrates the identification of a specific E3 that is responsible for recognition of pIκB polypeptides.

pIκBα-ubiquitin conjugation and degradation requires a full complement of the ubiquitin system enzymes: E1, a specific E2 derived from the ubiquitin system fraction I, E2F1 (Alkalay et al., *Proc. Natl. Acad. Sci. USA* 92:10599, 1995; Chen et al., *Cell* 84:853, 1996) and a Fraction II-component E3. To identify the ubiquitin system component involved in the substrate recognition, HeLa lysate was fractionated over IκBα phosphopeptide modulating agent columns, and the flow-through fractions were assayed for pIκBα conjugation. Peptides were coupled to NHS-Sepharose® (Pharmacia) according to the manufacturer's instructions at a concentration of 2 mg/ml. 100 μg of HeLa extract were incubated with 2.5 μl coupled resin in the presence of 0.1% NP40 and 3% ovalbumin for 1 hour at 4° C. The resin was discarded and the unbound material tested in the ubiquitination assay described above.

Figure 3A:
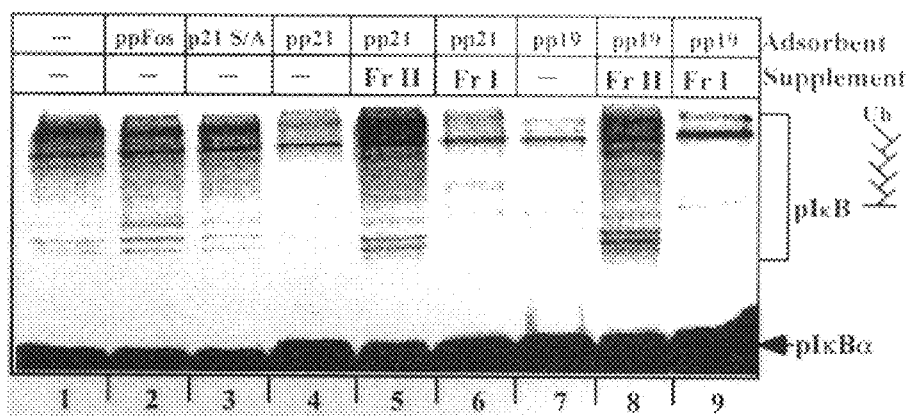
FIG. 3A is an autoradiogram depicting the results of SDS-PAGE analysis of ubiquitination assays performed using flow-through fractions of HeLa cell lysate fractionated over modulating agent columns. In each case, the substrate was a $^{35}$-labelled, HA-tagged IκBα polypeptide (SEQ ID NO:12) that was phosphorylated and NF-κB complex-associated. Lane 1 shows the level of ubiquitination using a non-fractionated extract. In lanes 2–9, the extract was fractionated over a peptide-Sepharose® column. The peptides used were: c-Fos phosphopeptide (ppFos (SEQ ID NO:10), lane 2); serine 32, 36 to alanine substituted IκBα peptide (pp21S/A (SEQ ID NO:11), lane 3); doubly phosphorylated IκBα peptide (pp21 (SEQ ID NO:9), lanes 4–6); and doubly phosphorylated IκBα peptide (pp19 (SEQ ID NO:8), lanes 7–9). In addition, reticulocyte Fraction II (160 μg) was added to the ubiquitination reactions shown in lanes 5 and 8, and Fraction I (160 μg) was added to the reactions in lanes 6 and 9.
Figure 3B:
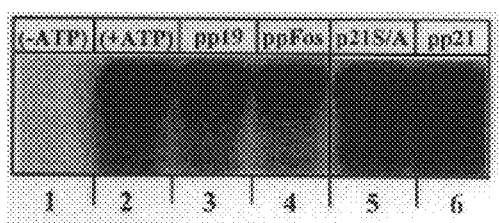
FIG. 3B is an autoradiogram showing the ubiquitination of bulk cellular proteins in HeLa extract. Lane 1 shows the ubiquitination in the absence of ATP, and lane 2 shows the ubiquitination in the presence of ATP, but without candidate modulating agent. In lanes 3–6, candidate modulating agents were added: 40 μM doubly phosphorylated IκBα peptide (pp19 (SEQ ID NO:8), lane 3); 400 μM c-Fos phosphopeptide (ppFos (SEQ ID NO:10), lane 4); 400 μM serine 32, 36 to alanine substituted IκBα peptide (pp21S/A (SEQ ID NO:11), lane 5); and 40 μM doubly phosphorylated IκBα peptide (pp21 (SEQ ID NO:9), lane 6).

Whereas a flow-through fraction from a control phosphopeptide column and an S32/36A peptide column retained full IκBα conjugation capacity (FIG. 3A, lanes 2, 3) flow-through fractions from two different pIκBα peptides lost their IκBα specific conjugation capacity (lanes 4, 7). The depleted conjugating activity could be complemented by reticulocyte Fraction II (lanes 5, 8) that contains all the known species of E3 enzymes (Ciechanover, *Cell* 79:13, 1994). Complementation could not be obtained by the addition of Fraction I or Fraction I and E1 (lanes 6 and 9, respectively), indicating that the peptide columns depleted an E3 rather than E2 or E1. Again, IκBα lysine residues 21 and 22 were dispensable for retaining the E3 (compare FIG. 3A, lane 7 to lane 4), emphasizing the distinction between the substrate recognition and conjugation site. The peptide column depletion was found to be specific for the IκB E3, as all flow-through fractions maintained full activity in random HeLa protein conjugation (as detected by measuring the conjugation of $^{125}I$ ubiquitin, FIG. 3B). This indicates that a specific E3 is responsible for recognition of the pIκBs at the identified motif.

Example 3

Effect of Representative Peptide Modulating Agents on Cellular NF-κB Activation

This Example illustrates the inhibition of cellular NF-κB activation by microinjection of peptide modulating agents.

HeLa cells were plated on a grid coverslips (Cellocate, Eppendorf) 18 hours before microinjection. Microinjection was performed with a 22 amino acid pIκBα peptide (pp21; Table I and SEQ ID NO:9) or a control phospho-Fos peptide (SEQ ID NO:10) using a semi-automated apparatus (Eppendorf). Peptides were injected into the cell cytoplasm at a concentration of 5 mg/ml in 100 mM KCl, 5 mM $Na_2HPO_4$ (pH 7.2), and immediately activated with TNFα (200 units/mL) for either 20 minutes (for NF-κB translocation) or 3 hours (for E-selectin expression). Following activation, the cells were fixed and stained with p65 specific antibodies (Mercurio et al., *Genes & Dev.* 7:705, 1993; Santa Cruz) or monoclonal anti-E-selectin antibodies (R&D Systems).

Figure 4A:
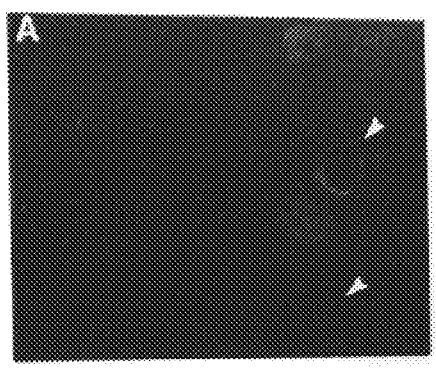
FIGS. 4A–4F are micrographs showing the effect of candidate modulating agents on nuclear NF-κB translocation.
Figure 4B:
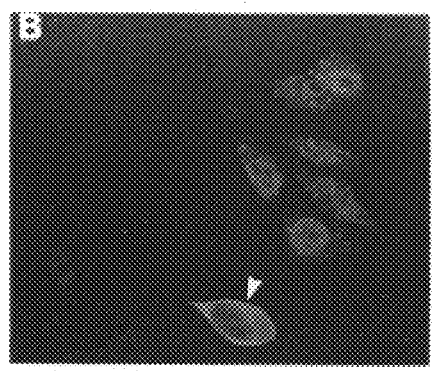
Figure 4C:
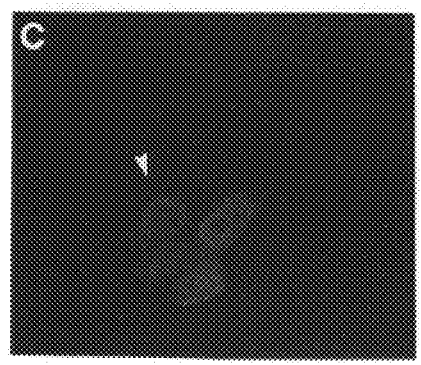
Figure 4D:
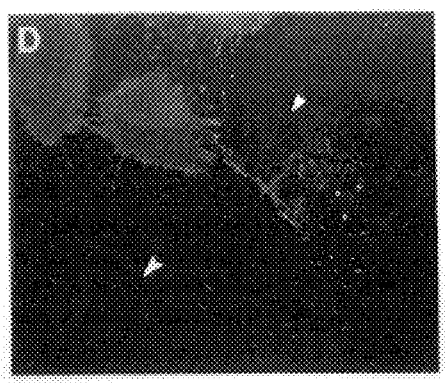
Figure 4E:
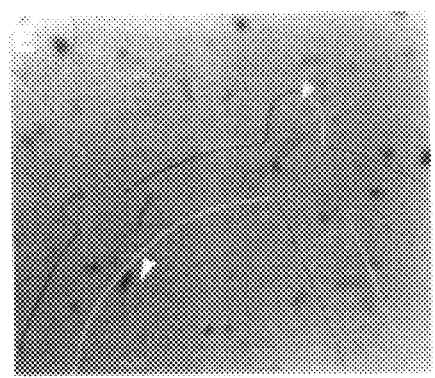
Figure 4F:
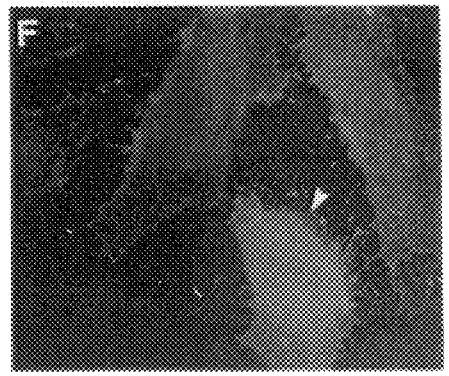
Figure 4G:
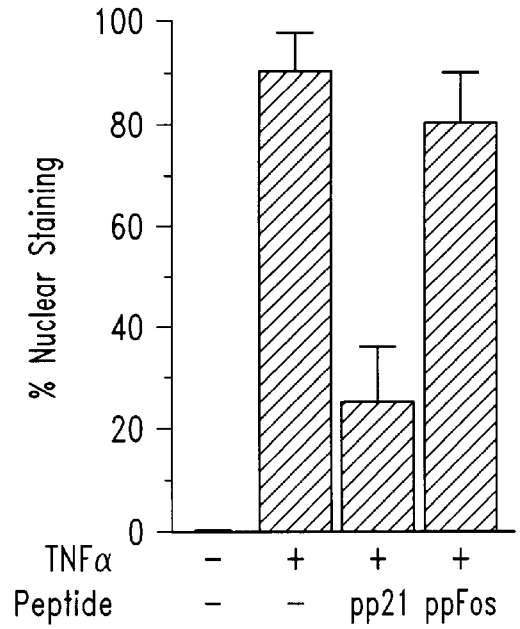
FIGS. 4G and 4H are graphs presenting a summary of the microinjection experiments shown in FIGS. 4A–4F.

In the absence of peptide modulating agent, TNFα induces rapid nuclear translocation of NF-κB into the nucleus, as shown by the p65 nuclear staining of 90% of the cells (see FIG. 4G, column 2). The pp21 peptide abolished TNFα-stimulated NF-κB activation in 50%–70% of the microinjected cells in several experiments (see representative fields in FIGS. 4A and 4B; and FIG. 4G, column 3). In contrast, the control pp-Fos peptide had no effect on the rate of NF-κB induced nuclear translocation, as compared to non-microinjected cells (FIGS. 4C and 4G, column 4).

Figure 4H:
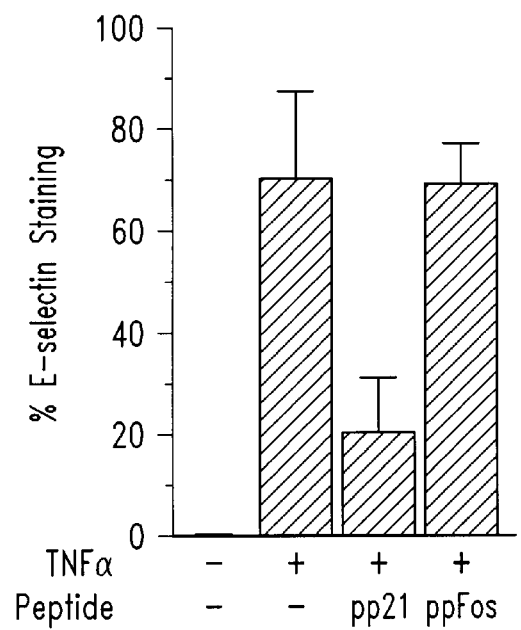

To further assess the functional consequences of NF-κB inhibition, the IκB-E3 inhibitory peptide was microinjected into primary human vascular endothelial cells (HUVEC; Chen et al, *J. Immunol* 155:3538, 1995). These cells respond to TNFα stimulation by surface expression of NF-κB regulated adhesion proteins, such as E-selectin. HUVEC cells were plated, microinjected and stimulated as described above. Three hours post stimulation the cells were fixed and stained for expression of the NF-κB dependent E-selectin. 75%–85% of the HUVEC cells were intensely stained for E-selectin following TNFα stimulation in several experiments. Microinjection of the pp21 peptide resulted in the inhibition of E-selectin expression in 70%–80% of the microinjected cells (FIG. 4D; and FIG. 4H, column 3). In contrast, the control pp-Fos peptide had no effect on E-selectin expression, as compared to non-microinjected cells (FIGS. 4F and 4H, column 4). Microinjection of a control, S32/36A substituted IκBα peptide had no effect on the rate of E-selectin expression (data not shown).

These results demonstrate that the subunit-specific degradation of the signal-induced phosphorylated IκBα0 and IκBβ is mediated by a specific E3. The recognition domain for E3 ubiquitin ligase is a short sequence, centered around the two signal-acquired phosphoserines conserved in both IκBs, representing the first biologically relevant E3 recognition motif. The specificity in IκB recognition is supported by the context of the phosphorylated substrate: an associated cellular complex masks the substrate from non-specific E3s. This feature restricts the NF-κB inhibitor degradation to the post-stimulation phase, at which it is exposed through site-specific phosphorylation event(s) to the specific ligase. NF-κB activation and its resultant function can be specifically abolished by in vivo inhibition of the IκB ligase, using a modulating agent as provided herein.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NO:1 is amino acid sequence of IκBα
SEQ ID NO:2 is DNA sequence of IκBα
SEQ ID NO:3 is amino acid sequence of IκBβ
SEQ ID NO:4 is DNA sequence of IκBβ
SEQ ID NO:5 is amino acid sequence of pp7

SEQ ID NO:6 is amino acid sequence of pp11
SEQ ID NO:7 is amino acid sequence of pp15
SEQ ID NO:8 is amino acid sequence of pp19
SEQ ID NO:9 is amino acid sequence of pp21
SEQ ID NO:10 is amino acid sequence of phospho-Fos peptide
SEQ ID NO:11 is amino acid sequence of pp21 S/A
SEQ ID NO:12 is amino acid sequence of HA-tagged IκBα
SEQ ID NO:13 is amino acid sequence of HA-tagged S32, 36 IκBα
SEQ ID NO:14 is amino acid sequence of HA-tagged IκBβ

We claim:

1. A method for identifying an agent that modulates ubiquitination of IκBα and/or IκBβ, comprising:
   (a) incubating a candidate agent with an IκB polypeptide and a cellular extract, wherein the step of incubating is carried out under conditions and for a time sufficient to allow phosphorylation of the IκB polypeptide and formation of a complex comprising phosphorylated IκB polypeptide and NF-κB; and
   (b) subsequently measuring the ability of the candidate agent to modulate ubiquitination of the complex, and therefrom identifying an agent that modulates ubiquitination of IκBα and/or IκBβ.

2. A method according to claim 1, wherein the agent is a peptide.

3. A method according to claim 2, wherein the peptide comprises a recognition domain for E3 ubiquitin ligase.

4. An agent that modulates ubiquitination of IκBα and/or IκBβ.

5. An agent according to claim 4, wherein the agent is a peptide.

6. An agent according to claim 5, wherein the agent comprises a recognition domain for E3 ubiquitin ligase.

7. An agent according to claim 6, wherein the agent comprises an amino acid sequence recited in at least one of SEQ ID NO:5–SEQ ID NO:9.

* * * * *